May 9, 1961 R. C. SCHIRING ET AL Re. 24,982

TUBULAR TELESCOPIC COLUMN

Original Filed July 8, 1954 2 Sheets-Sheet 1

INVENTORS.
RALPH C. SCHIRING
EDGAR J. BASTIN
BY
Hyde, Meyer, Baldwin & Doran
ATTORNEYS

TUBULAR TELESCOPIC COLUMN

Original Filed July 8, 1954 2 Sheets-Sheet 2

INVENTORS.
RALPH C. SCHIRING
EDGAR J. BASTIN
BY
Hyde, Meyer, Baldwin & Doran
ATTORNEYS United States Patent Office Re. 24,982
Reissued May 9, 1961

24,982

TUBULAR TELESCOPIC COLUMN

Ralph C. Schiring, Shaker Heights, and Edgar J. Bastin, Chesterland, Ohio, assignors to Picker X-Ray Corporation Waite Manufacturing Division, Inc., Cleveland, Ohio, a corporation of Ohio Original No. 2,835,520, dated May 20, 1958, Ser. No. 441,994, July 8, 1954. Application for reissue May 19, 1960, Ser. No. 30,721

5 Claims. (Cl. 287—58)

Matter enclosed in heavy brackets [ ] appears in the original patent but forms no part of this reissue specification; matter printed in italics indicates the additions made by reissue.

This invention relates to telescopic structures and more particularly to tubular telescopic columns.

An object of this invention is to provide a telescopic structure made up of a plurality of slidably, interfitted concentric cylindrical tubes having a plurality of rollers dispersed between the various tube surfaces to facilitate axial movement between the various tubes and thereby assure easy and precise adjustment.

Another object is to provide a telescopic structure as described above, wherein the rollers facilitate axial movement but prevent any circumferential rotation of the tubes with respect to one another.

Still another object of this invention is to provide a relatively light-weight, heavy-duty telescopic structure which is capable of supporting large loads without danger of distorting or bending.

A further object is to provide a telescopic column wherein there is a minimum of friction between the working elements thereby cutting down on wear and replacement of parts.

Another object of the present invention is to provide a telescopic structure characterized by its structural simplicity, the ease of assembly of its parts, its strong and sturdy nature, and its low manufacturing cost. Other features of this invention reside in the arrangement and design of the parts of carrying out their appropriate functions.

Other objects and advantages of this invention will be apparent from the accompanying drawings and description, and the essential features will be set forth in the appended claims.

In the drawings Fig. 1 is a side elevational view of my novel tubular telescopic column when used as a support or carriage for an X-ray tube.

Figure 1:
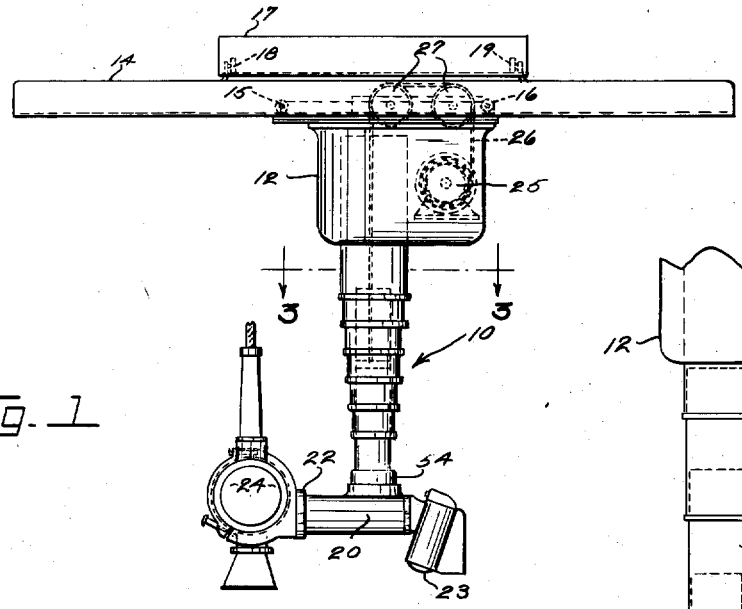

Although our tubular telescopic column has application in many places we have chosen to illustrate the same as applied for the support of X-ray tubes. As seen in Fig. 1, the tubular telescope column 10 is suspended from an overhead tube stand 12 which is in turn portably mounted on channel members 14 by means of rollers 15 and 16. The channels 14 are in turn portably mounted on track members 17 by means of rollers 18 and 19. Thus, is will be seen that the channels 14 and tracks 17 provide a carriage upon which the telescopic column can be moved in two different directions while remaining in the same horizontal plane. At the lower end of the tubular column is mounted a hollow tubular member 20, through which extends a hollow tubular axle having a bracket at one end of the tubular member 20 and a suitable focusing light 23 at the other. The bracket 22 carries the X-ray tube itself, as indicated at 24. The bracket 22 and X-ray tube are rotatable about the tubular axle, while the X-ray tube 24 is oscillatable through another plane about bracket 22. For purposes of automatically raising and lowering the tubular column 10 an electric motor 25 is provided on or adjacent to the tube stand 12; connected therewith is a flexible member 26 which is trained over the guide pulleys 27 contained upon the upper surface of tube stand 12 and which then extends downwardly through the hollow center of the tubular column to a point where the other end of the flexible member is connected by suitable securing elements to the inner and lowermost tubular member of the telescopic column.

Figure 3:
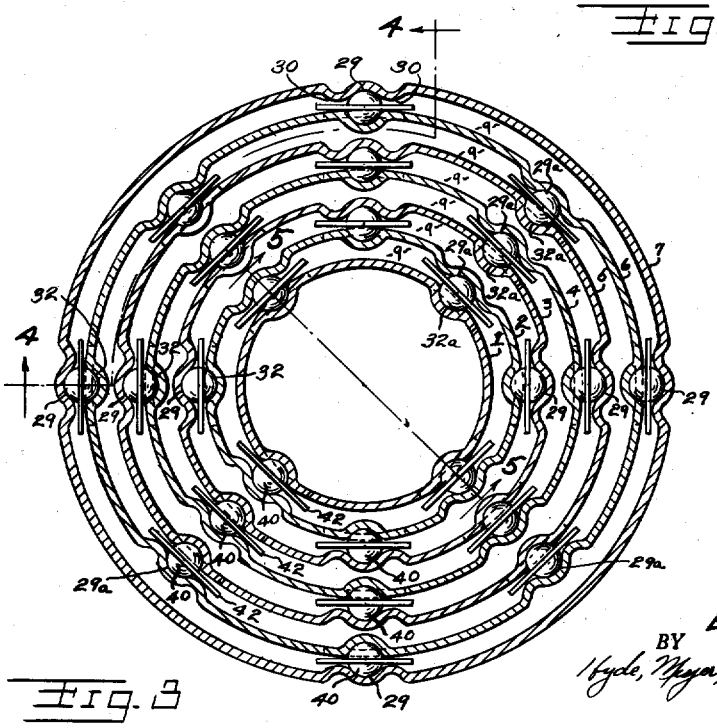
Fig. 3 is an enlarged horizontal cross-sectional view taken along the line 3—3 at the top of the telescopic column with all of the tubes completely collapsed or retracted.

Referring now to Fig. 3, there is shown a transverse sectional view of the telescopic column. The column is made up of a plurality of slidably interfitted concentric cylindrical tubes. Although we have shown seven tubes disposed one within another, it should be understood that we do not wish to limit the present invention to any particular number of tubes. The inside diameter of each tube is greater than the outside diameter of the next innermost tube, so that annular hollow chambers 9 are formed between adjacent tubes. The difference in the diameters is such that the tubular members slide within one another with a substantial clearance between their wall surfaces. This avoids accurate machining of complementary cylindrical surfaces on mating tubes as in the prior art. The outermost tube 7 is provided with four longitudinally extending grooves 29 on its inner surface. It should be noted that the grooves 29 are not cut out of the material of the tube 7, but rather are formed by bending or curving the entire thickness of the tube wall to a suitable conformation which defines the grooves. Each of the alternate concentric tubes 7, 5 and 3 is provided with similar grooves 29 on their inner surfaces. The grooves 29 on the inner surfaces of each of the tubes 7, 5 and 3 are provided by first bending the tube surfaces to curve slightly inwardly and forming projecting portions 30 which extend into the chambers 9. A reverse outward bend in the material of the tube intermediate the projecting portions 30 forms the central arcuate portion of each of the grooves 29. The outermost surface of the material forming the arcuate portion of each groove 29 is in alignment with the outer circumferential surface of the tubes 7, 5 and 3. The inwardly projecting portions 30 extend inwardly substantially to the radially mid-point of the chambers 9. In radial alignment with the grooves 29 contained on the inner surfaces of alternate concentric tubular members 7, 5 and 3, we have provided grooves 32 on the outer surface of each the remaining concentric tubes 6, 4 and 2. The grooves 32 are contained on the outer surface of the tubes 6, 4 and 2 and are formed by bending the surface of said tubes inwardly to form a groove having an arcuate portion (in section) of substantially the same radius as that of groove 29.

Figure 4:
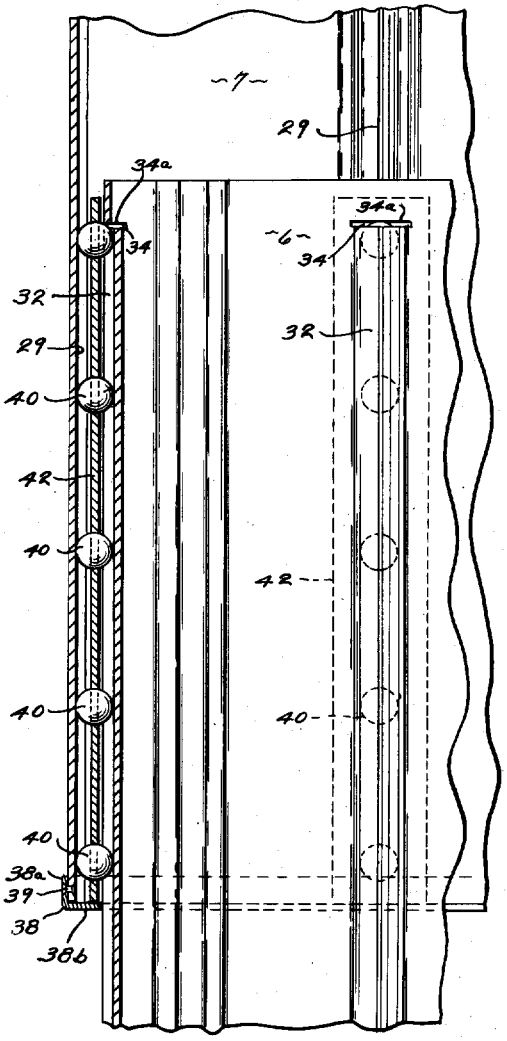
Fig. 4 is an enlarged fragmental sectional view taken along the line 4—4 of Fig. 3.

The remaining concentric tubes 6, 4 and 2 are provided with longitudinally extending grooves 29a on their inner surfaces. The grooves 29a are spaced equal circumferential distances from the adjacent longitudinally extending grooves 29 on the inner surfaces of the alternate concentric tubes 7, 5 and 3. The grooves 29a on the inner surfaces of the remaining concentric tubes 6, 4 and 2 are identical in construction to the grooves 29 on the inner surface of alternate concentric tubes 7, 5 and 3. The alternate concentric tubular members 5, 3 and 1 are seen to contain longitudinal extending grooves 32a on their outer surfaces in complementary relationship and in radial alignment with the grooves 29a on the inner surfaces of members 6, 4 and 2. The grooves 32a on the outer surfaces of members 5, 3 and 1 are identical in construction to the grooves 32 on the outer surfaces, of members 6, 4 and 2. Thus, it will be seen that each concentric tube, with the exception of the outermost and innermost tubes, 7 and 1 respectively, is provided with alternate grooves (32 or 32a) and (29 or 29a) respectively, each spaced circumferentially substantially forty-five degrees apart. The outermost tube 7 contains only grooves 29 on its inner surface, while the innermost tube 1 contains only grooves 32a on its outermost surface. Referring to Fig. 4, it will be seen that the distal ends of the longitudinally extending grooves (32, 32a) terminate short of the ends of their respective concentric tubes. The upper end of the grooves 32, 32a is seen to contain a slot 34 cut into the surface of the respective tubes a spaced distance from the upper end of said tubes. The slots 34 have a length slightly greater than the width of groves 32 and 32a and are disposed substantially perpendicular to the longitudinal axis of said grooves. The slot 34 provides an abutment in the form of edge wall 34a which sharly terminates the upper end of the grooves. The lower end of each longitudinally extending groove is terminated by an annular retaining rim 38 surrounding the lower outer end of each tubular member. The rim member 38 has a vertically extending annular flange 38a which is fastened to the side wall of each tubular member 2 to 7 by means of rivets 39 and an annular flange portion 38b extending inwardly for slidably engaging the outer surfaces of the next smaller tubular member 6.

The parallel longitudinally extending grooves (29, 29a) and (32, 32a) give the tube a corrugated effect and serve as reinforcing ribs which greatly increase the structural rigidity and overall strength of the tubular column.

The complementary grooves (29 and 32) and (29a and 32a) between adjacent surfaces of the various tubes form races for supporting suitable bearings. A plurality of ballbearings 40 are contained in the annular concentric chambers 9 and are supported between the surfaces of adjacent tubes by the races formed by the complementary grooves. As seen in Fig. 4, a plurality of ball-bearings 40 are arranged in axial alignment within each pair of complementary grooves (29 and 32). A spacer cage 42 made up of an elongated rectangular member containing a plurality of spaced apertures maintains the axially aligned ballbearings 40 at an even spacing, as best seen in Fig. 4. During use, the axially aligned ball-bearings are contained within the various pairs of complementary grooves (29 and 32) and (29a and 32a) by having the upper end of the grooves turned outwardly at point 34, as described above, and at the lower end by the retaining annular rim member 38. The total axial extent of the ball-bearings 40 and cage member 42 is always substantially less than the axial extent of the complementary grooves (29 and 32) and (29a and 32a) to allow for telescopic movement between the various concentric tubes. With reference to Fig. 3, it will be seen that the various axially aligned ball-bearings are radially aligned at varying angles circumferentially of the tubular column 10. Each of the ball-bearings 40 is supported at two zones on its surface by the complementary pairs of grooves. Each ball is free to rotate within the cage member 42 and moves along the arcuate surfaces of the complementary grooves as the telescopic tubular members are extended and contracted.

Figure 2:
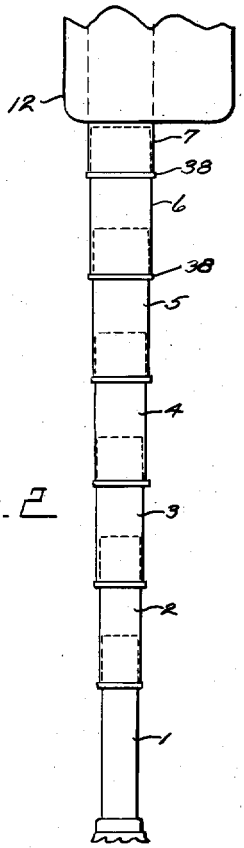
Fig. 2 is an elevational view of the depending telescopic column of Fig. 1 in a substantially fully extended position.

The provision of a plurality of axially aligned ball-bearings 40 which roll between adjacent concentric tube surfaces greatly reduces the area of contacting surface and friction between the concentric tubes and very little resistance is offered to the telescopic movement of the tubes. While presenting very little bearing surface the roller bearings are axially spaced over a distance great enough to provide adequate support over a substantial zone between adjacent tubes to prevent wobbling and distortion between the various tubes and thereby insure an accurate and precise movement of the supported load. It will be seen in Fig. 4 that adjacent concentric tubes cannot be fully extended, end to end, with respect to each other due to the bearings 40 and cages 42 extending axially between the tubes and abutting the annular rim 38 at the lower end of the outer tube 7 and the edge wall 34a at the upper end of groove 32 on the inner tube 6. For this reason adjacent concentric tubes will always overlap one another, even when fully extended, as seen in Fig. 2 and thereby insure a rigid column at all times.

Although the ball-bearings 40 may move axially within their respective grooves or races, there can be no circumferential movement of the bearings within the chambers 9 since they are constrained between complementary pairs of grooves between adjacent concentric tubes. The concentric tubes cannot move circumferentially with respect to one another due to the locking action between the ball-bearings and grooves.

Thus, the ball-bearings serve a three-fold function. First, by reducing friction during telescopic movement of the concentric tubular members; second, by maintaining proper spacing between the surfaces of the adjacent tubular members and insuring precise movement; and thirdly, by preventing circumferential rotation between the respective concentric tubes.

Figure 6:
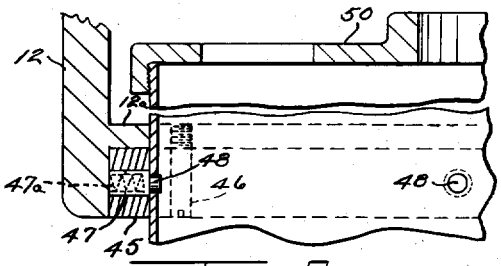
Fig. 6 is an enlarged vertical fragmental sectional view of the fastening means between the top tube of the telescopic column of Fig. 1 and the overhead column support housing.

Referring now to Fig. 6, I have shown a detailed view of the manner in which the tubular telescopic column 10 is secured to the tube housing 12. The tube housing 12 contains an annular horizontal inwardly extending flange 12a on its inner surface at a spaced distance from the lower edge of the housing. An annular ring 45 is secured to the flange by means of screws 46 which engage the flange 12a. The annular ring 45 has its innermost surface flush with that of flange 12a, and its lowermost surface flush with the lower end of the tube housing 12. The annular ring 45 contains four equally spaced spring pressed pins each comprising a cylindrical housing portion 47 containing a spring 47a, and a projecting pin portion 48 which engages one of four apertures contained in the side walls of the outermost concentric tube member 7, adjacent the upper end of the tube. The upper end of the outermost concentric tube 7 is provided with a cap member 50 which is threadedly secured to the tube 7. The cap 50 is provided with an aperture in its center, through which extends the flexible member 26.

Figure 5:
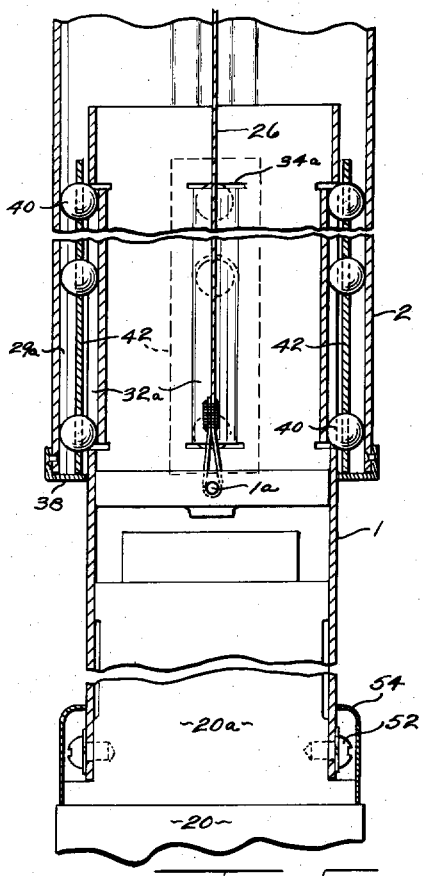
Fig. 5 is a fragmental view taken along the plane of line 5—5 of Fig. 3.

Referring now to Fig. 5, the innermost concentric tube 1 containing only grooves 32a on its outer surface, as seen in Fig. 3, is fastened to the flexible member 26 by means of pin 1a, which is secured between the inner side walls of the tube 1. The X-ray tube head 24 and its associated focussing light 23 are fastened to the lower and concentrically innermost tube 1 by means of hollow tubular housing 20. The tubular housing 20 has an upwardly extending central portion 20a which has an outer diameter less than the inner diameter of the concentric tube 1, and is telescopically inserted within the lower end of tube 1, as seen in Fig. 5, and retained therein by screws 52 which extend through the side wall of the tube 1 and embed themselves within the upstanding portion 20a. For aesthetic purposes an annular rim 54 is secured to the hollow tubular housing 1 and covers the screws 52.

In the operation of the device it will be readily apparent that the weight of the X-ray tube head itself will normally tend to lower itself by extending to the telescopic tubular tubes. It is therefore only necessary to provide mechanical means for raising the X-ray tube. By actuating motor 25 and rewinding the flexible member 26 the concentric tubes of the column will be drawn upwardly into a collapsed position, carrying within them the X-ray tube, as seen in Fig. 1. When lowering the X-ray tube it is only necessary for the operator to reverse the motor 25 so as to play out the flexible member 26 and permit the weight of the X-ray tube itself to carry the apparatus downwardly, to an extended position as shown in Fig. 2.

In view of the foregoing description, taken in conjunction with the accompanying drawings, it is believed that a clear understanding of the construction, operation, and advantages of the device will be quite apparent to those skilled in this art. It is to be understood, however, that even though there is herein shown and described a preferred embodiment of the invention, the same is susceptible to certain changes fully comprehended by the spirit of this invention.

What we claim is:

1. A telescopic structure comprising inner and outer slidably interfitted concentric generally cylindrical tubes of sheet material of substantially uniform thickness, the inside diameter of the outer tube being greater than the outside diameter of the inner tube thereby forming a generally annular chamber between said tubes, axially extending grooves formed in said sheet material, said grooves being spaced circumferentially about said tubes, said grooves on said inner tube being concave outwardly, said grooves on said outer tube being concave inwardly, said grooves on said tubes mutually facing each other, a plurality of ball bearings in said grooves, said bearings being of a diameter to fill snugly the space between each pair of mutually facing grooves and holding said tubes free of direct contact, an axially movable cage for said bearings disposed in said annular chamber between said tubes, and means preventing escape of said bearings endwise of said grooves, whereby said bearings hold said tubes concentric without appreciable play and reduce friction during relative telescoping movement between said tubes and prevent circumferential rotation between said tubes, while said grooves reinforce said tubes against bending under beam loading.

2. A telescopic structure comprising at least three slidably interfitted concentric generally cylindrical tubes of sheet material of substantially uniform thickness, the inside diameter of each tube being greater than the outside diameter of the next tube inwardly therefrom thereby forming a generally annular chamber between adjacent tubes, axially extending grooves formed in said sheet material, said grooves being equiangularly spaced circumferentially about said tubes, said grooves on each tube being alternately concave inwardly and concave outwardly whereby adjacent tubes may be oriented with an inwardly concave groove of each tube facing an outwardly concave groove of an adjacent tube, thereby forming bearing races of which the races between an inner and an intermediate tube are staggered circumferentially with respect to the races between said intermediate tube and an outer tube, a plurality of anti-friction bearings in said races, each of said bearings having an axis of rotation at right angles to the radii of said tube, said bearings being of a diameter to fill snugly the space between each pair of mutually facing grooves and holding said tubes free of direct contact, an axially movable cage for said bearings disposed in said annular chamber between said tubes, and means preventing escape of said bearings endwise of said grooves, whereby said bearings hold said tubes concentric without appreciable play and reduce friction during relative telescoping movement between said tubes and prevent circumferential rotation between said tubes, while said grooves reinforce said tubes against bending under beam loading.

*3. In a tubular telescoping apparatus adaptable to be connected at one end to a support and at the other end to a weight to support said weight from said support the combination of, at least three relatively reciprocable tubes telescoped together in axial alignment, one of said tubes being a first end tube, another of the tubes being a second end tube, each remaining tube being an intermediate tube having inner and outer surfaces; each such intermediate tube outer surface having a plurality of longitudinally extending, circumferentially uniformly spaced, concave grooves therein each of which is parallel to the axis of the tube; each such intermediate tube inner surfaces having a plurality of longitudinally extending, circumferentially uniformly spaced, concave grooves therein each of which is parallel to the axis of the tube; each such intermediate tube having a like number of grooves in the inner and outer surfaces, each of said outer surface grooves each being spaced circumferentially midway between two inner surface grooves, said first end tube having an inner surface with a plurality of longitudinally extending, circumferentially spaced, concave grooves therein paralleling the axis thereof; said second end tube having an outer surface having a plurality of longitudinally extending, circumferentially spaced, concave grooves therein paralleling the axis thereof; each such outer surface groove being paired with an inner surface groove on a contiguous tube, a plurality of bearing assemblies each including a group of ball bearings between each of the grooves of each such pair and in rolling abutment therewith, each bearing assembly also including an elongated bearing race maintaining the balls of each group in spaced relationship, and said tubes including stop means to limit extending relative travel.*

*4. In the device of claim 1 wherein said stop means includes a projection means extending in one radial direction at the base of the first end tube and at the base of each intermediate tube and a projection means extending in the other radial direction adjacent the top of the second end tube and each intermediate tube.*

*5. The device of claim 4 wherein each such projection means extending in said one radial direction comprises an annular flange abutted by the one end of each race when the tube is extended and each projection means extending in said other direction is a groove end abuttable by one of the balls when the tube is extended.*

References Cited in the file of this patent or the original patent

UNITED STATES PATENTS

| | | |
|---|---|---|
| 206,093 | Deschamp | July 16, 1878 |
| 311,224 | Bohner | June 27, 1885 |
| 701,042 | Holmes | May 27, 1902 |
| 1,359,790 | Campbell | Nov. 23, 1920 |
| 2,605,622 | Anderson | Aug. 5, 1952 |